United States Patent [19]
Schwaegerle

[11] Patent Number: 5,907,387
[45] Date of Patent: May 25, 1999

[54] MEDICAL INSTRUMENT SUPPORT MECHANISM

[75] Inventor: Gary G. Schwaegerle, Cincinnati, Ohio

[73] Assignee: Reliance Medical Products, Inc., Mason, Ohio

[21] Appl. No.: 09/065,140

[22] Filed: Apr. 23, 1998

[51] Int. Cl.[6] ................................................. A61B 3/00
[52] U.S. Cl. .......................................................... 351/200
[58] Field of Search ................................ 351/57, 200, 58; 33/299; 294/139; 297/186; 346/145; 312/209, 294, 310, 311; 248/121, 122.1; 224/185

[56] References Cited

U.S. PATENT DOCUMENTS

| 228,645 | 6/1880 | Kells, Jr. |
| 1,184,503 | 5/1916 | Alden. |
| 1,556,413 | 10/1925 | Buettner. |
| 1,795,296 | 3/1931 | De Zeng. |
| 3,122,348 | 2/1964 | Wilkinson. |
| 4,208,028 | 6/1980 | Brown et al. ............ 224/185 |
| 4,572,594 | 2/1986 | Schwartz ............ 312/209 |
| 4,905,711 | 3/1990 | Bennett et al. |
| 5,626,322 | 5/1997 | Braun. |
| 5,652,636 | 7/1997 | Feinbloom ............ 351/58 |

OTHER PUBLICATIONS

Marco Ophthalmic, *Delux Stands and Arms*, Leaflet, undated.
Topcon Corporation, *Ophthalmic Chairs and Stands*, Brochure, undated.
Reliance Medical Products, Inc., *Reliance 7000 Ophthalmic Wall Units*, Leaflet, undated.

Primary Examiner—George Manuel
Attorney, Agent, or Firm—Wood, Herron & Evans, L.L.P.

[57] ABSTRACT

A medical instrument support mechanism, particularly suitable for ophthalmological instruments, including first and second support arms and a suitable base member in which the first arm is vertically pivotal with respect to the base member and the base member is pivotal with respect to another support member, such as a support pole. The second arm is also pivotally connected to the first arm. A locking mechanism is operatively connected to each of the pivot connections to allow an operator to selectively lock and unlock the pivot connections substantially simultaneously by operating a lever movable in a direction extending along the length of the first support arm. This lever is preferably disposed along a lower side of the first support arm and specifically operates screw locking mechanisms and respective clamp members.

39 Claims, 7 Drawing Sheets

MEDICAL INSTRUMENT SUPPORT MECHANISM

FIELD OF THE INVENTION

This invention generally pertains to medical instrument support apparatus and, more particularly, to instrument support mechanisms that are used to hold ophthalmic or optical instrumentation to allow easy movement between different positions relative to a patient.

BACKGROUND OF THE INVENTION

Many different types of instrument support mechanisms exist in the medical industry for supporting medical instrumentation in front of a patient. Often, the patient is seated in an examination chair. As examples, ophthalmic instruments such as slit lamps, indirect ophthalmometer and vision tester must be placed in front of a patient during eye examination procedures while the patient is seated in an examination chair. These instruments are typically placed on a movable table or on movable instrument support arms mounted adjacent the patient. Instrument support arms are generally attached to support poles forming part of an instrument stand. In some systems, two arms may be used with one arm supporting lighter weight instruments and the other arm supporting heavier weight instruments. Heavier weight instrumentation may also be supported on the movable tables mentioned above.

Support mechanisms that have taken the form of arms which move with multiple degrees of freedom. A typical support mechanism may, for example, rotate about the support pole and move up and down along the support pole. The mechanism may also have a first arm which adjusts vertically using a pivotal motion and have a second arm at an outer end which is pivotally connected to the first arm. Additional arms or support structure may be connected to the arms.

Each of the above described movements should be lockable such that a practician may set the mechanism and, therefore, the attached instrumentation in the desired location relative to the patient. Certain instrument arms are not lockable, however, this is not desirable in many situations. Most arms in the past have required at least two separate lock mechanisms and two separate manually operated levers or knobs to lock and unlock the various pivot connections of the mechanism. This makes locking and unlocking the mechanism cumbersome and often difficult for the practician. One known type of instrument support mechanism does include a single lever for locking and unlocking the three main pivoting movements described above. However, this lever must be rotated generally in a direction perpendicular to the mechanism. Therefore, the practician must use two hands to hold the mechanism against rotation about the support pole while rotating the lever to lock the mechanism in place. The same holds true when unlocking the mechanism. Also, the levers and knobs as previously located on such mechanisms may not be easily accessed or actuated by the practician.

For the reasons stated above as well as other reasons, it would be desirable to provide an adjustable medical instrument support mechanism, and especially a mechanism suitable for use in the ophthalmic area, in which a simplified and easily actuated locking mechanism is used and includes a single lever which may be actuated in a simple motion to either lock or unlock various pivot connections of the support mechanism.

SUMMARY OF THE INVENTION

The present invention therefore provides a medical instrument support mechanism which includes a unique locking mechanism allowing easier use by a practician. The mechanism is especially suitable for use in the ophthalmic or ophthalmologic industry but could be used in other medical areas as well. More specifically, the instrument support mechanism of this invention includes a base member which could be a stationary support, such as a pole, or a separate member connected to a pole. A first support arm is connected to the base member and a second support arm is connected to the first support arm. The first support arm is connected to the base member by a pivot connection at one end allowing the other end to be moved with respect to the first end. This movement preferably is a vertical, pivotal motion but could alternatively or additionally comprise a pivoting motion about the base member. The second arm is also preferably connected by a pivot connection to the first support arm to allow the second support arm to swing about an axis relative to the first support arm. In the preferred embodiment, the base member is connected to a vertical support pole for rotation about the pole and height adjustment along the pole.

In accordance with the invention, a locking mechanism is uniquely connected to two or more pivot connections to allow an operator to selectively lock and unlock the pivot connections. More specifically, the locking mechanism is operated by a lever which is movable in a direction extending along the length of the first support arm. This helps ensure that pivoting motion does not occur while locking or unlocking the mechanism. More preferably, the lever is disposed along an underside of the first support arm and is operated by a simple push/pull movement.

More specifically, the locking mechanisms of this invention are advantageously designed as unique screw locking mechanisms. Each screw locking mechanism locks and unlocks to at least one pivot connection by operating a clamp member associated therewith. The clamp members used in the present invention may be generally U-shaped clamp members that receive an element of the pivot connection. In the case of the vertically adjustable pivot connection, the screw clamps or unclamps linkage members associated with the vertically adjustable pivot connection. Also in accordance with the invention, the screws used in the screw locking mechanisms are preferably double helical threaded screws. While single lead screws will function, the use of double lead screws shortens the required travel of the actuating lever.

In accordance with the preferred embodiment of this invention, heavy duty and light duty instrument support mechanisms are constructed in accordance with the invention. In a heavy duty version of a medical instrument support mechanism, for example, multiple counterbalancing springs may be used in place of a single counterbalancing spring and heavier duty and/or larger numbers of linkage members may be used to support the heavier instrumentation. In each case, the broader principles of this invention may be employed to achieve the advantages of the invention.

These and other object and advantages of the invention will be more readily apparent to those of ordinary skill in the art upon review of the following detailed description of the preferred embodiments taken in conjunction with the accompanying drawings.

BRIEF DESCRIPTION OF THE DRAWINGS

FIG. 2A is a cross sectional view taken along line 2A—2A of FIG. 2;

DETAILED DESCRIPTION OF THE PREFERRED EMBODIMENTS

Figure 1:
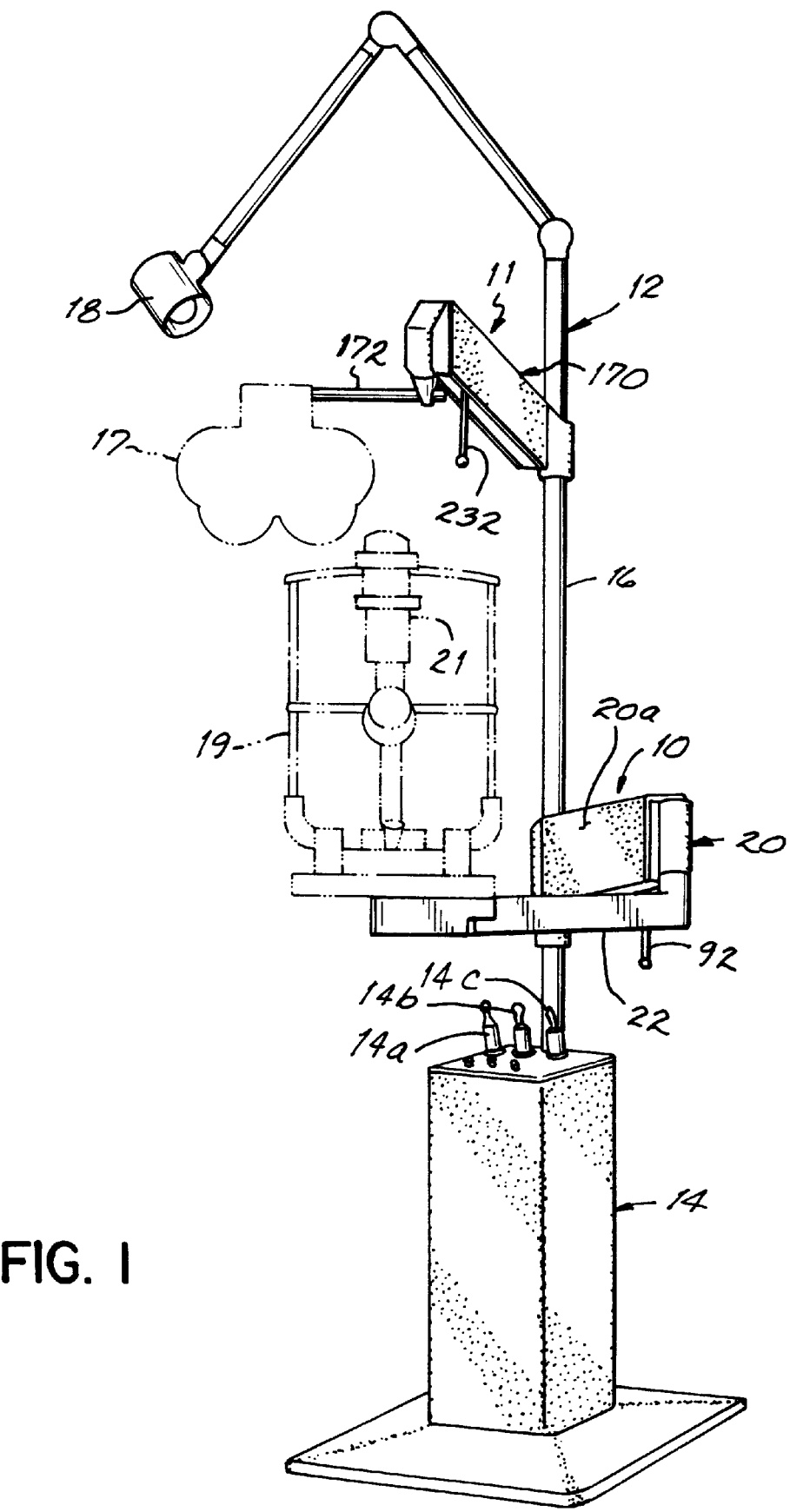
FIG. 1 is a perspective view of an illustrative instrument stand showing the use of both heavy duty and light duty instrument support mechanisms of the present invention.

FIG. 1 illustrates a typical ophthalmic instrument system showing one potential use for a heavy duty support mechanism 10 and a light duty support mechanism 11, each being constructed in accordance with principles of this invention. Mechanisms 10, 11 are shown affixed to one type of instrument stand 12, however, it will be understood that many other supports may be used for mechanisms 10 and 11, as shown in FIG. 1, or mechanisms taking other forms in accordance with the invention. Instrument stand 12 generally includes a base 14 which may hold a plurality of instruments 14a, 14b, 14c and which includes an upwardly extending pole 16. Pole 16 may have an overhead light 18 attached at the upper end. As further shown in dotted lines in FIG. 1, support mechanism 11 may carry a lighter weight ophthalmic instrument, such as a vision tester 17, while mechanism 11 may carry heavier weight structure such as a chin rest 19 and a slit lamp 21 or other instrument (not shown).

Figure 2:
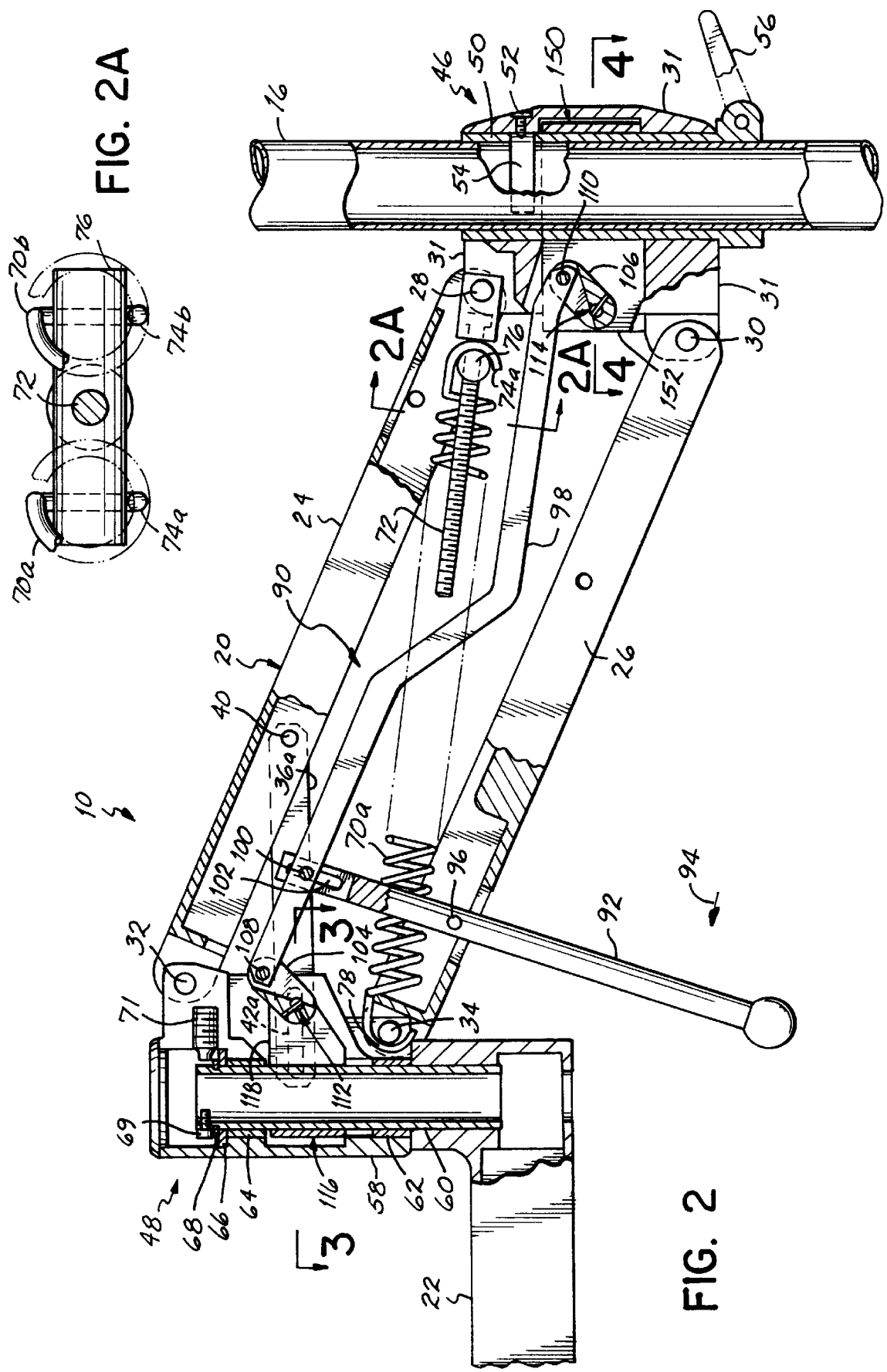
FIG. 2 is a partially fragmented side elevational view of the heavy duty instrument support mechanism shown in FIG. 1 showing the mechanism in a locked position.
Figure 3:
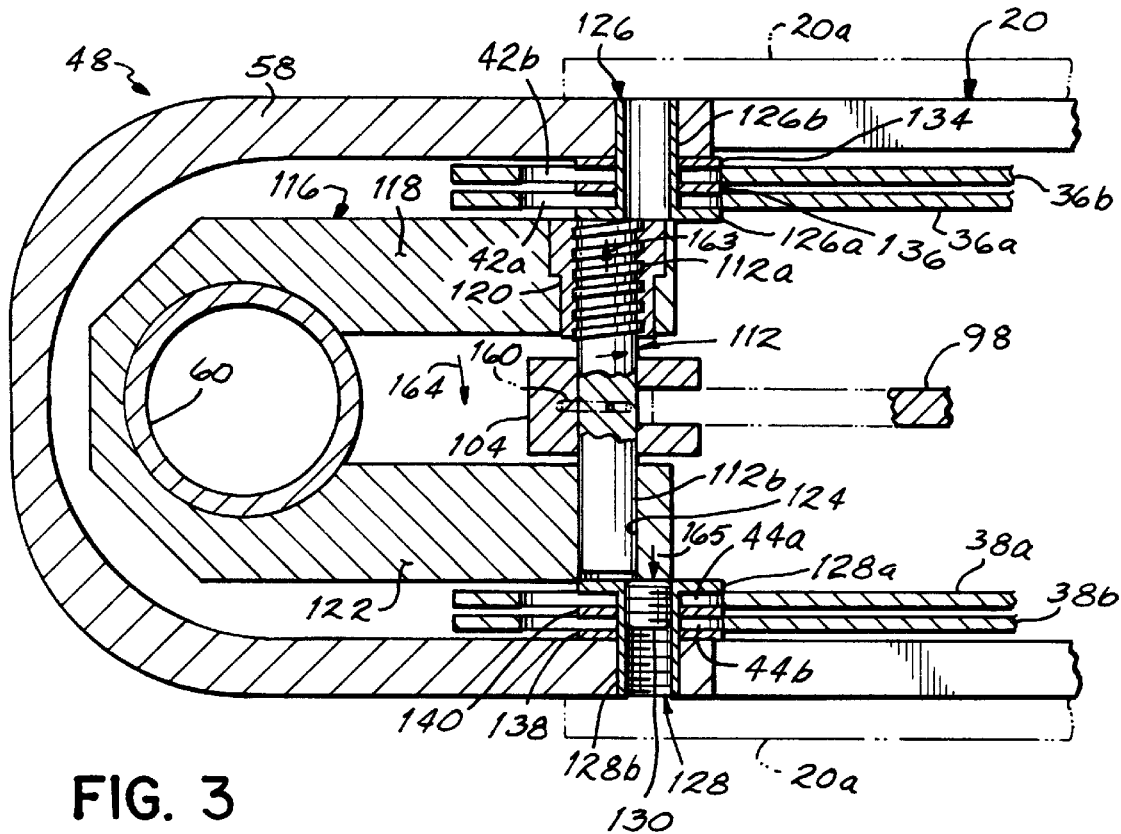
FIG. 3 is a cross sectional view taken along line 3—3 of FIG. 2.

Referring now to FIG. 2, instrument support mechanism 10, which is suitable for heavier duty applications, includes a first arm 20 and a second arm 22 pivotally connected together by means to be described below. A cover 20a is preferably used to conceal the internal components and conventional wiring (not shown) associated with arm 20. A similar cover may be used on arm 11 (FIG. 1) as mentioned below. First arm 20 comprises a first link member 24 and a second, lower link member 26. Link members 24, 26 are respectively affixed by pivots 28, 30 to a base member 31. These pivots 28, 30 allow the opposite end of arm 20 to be moved vertically with respect to base member 31. Referring briefly to FIG. 3, respective pairs of links 36a, 36b and 38a, 38b assist with the locking of arm 20 in a desired vertical orientation relative to base member 31. In this regard, links 36a, 36b and 38a, 38b are pivotally connected to first link member 24. One pivot 40 for securing one end of links 36a, 36b is shown in FIG. 2 with the understanding that a similar pivot connects links 38a, 38b to the same link member 24. As best shown in FIG. 3, the opposite ends of links 36a, 36b and 38a, 38b include respective slots 42a, 42b and 44a, 44b for reasons to be described below.

Still referring to FIG. 2, along with the vertical pivoting movement allowed by the pivoting nature of link members 24, 26, first arm 20 may pivot about support pole 16 by a pivot connection 46 and second arm 22 may pivot with respect to both the first arm 20 and support pole 16 by a pivot connection 48. More specifically, pivot connection 46 is made by way of a tube 50 that may be rigidly locked to support pole 16 and which receives a portion of base member 31 thereabout. To act as a stop for pivoting motion about pole 16, a screw 52 is contained in base member 31 and extends into a slot 54 contained in tube 50. A conventional screw operated clamp mechanism 56 is used to secure tube 50 rigidly to pole 16. When lock 56 is in an unlocked position, tube 50 and the attached mechanism 10 may be height adjusted along support pole 16.

At the opposite end of first arm 20, pivot connection 48 more specifically comprises a pivot support 58 which holds a pivot tube 60 for rotation therein. Pivot tube 60 is held for rotation within bearing members or low friction bushings 62, 64. A retaining ring 68 holds pivot tube 60 in place within pivot support 58. Retaining ring 68 rests against a washer 66 as shown in FIG. 2, to keep second arm 22 held in place within pivot support 58. Pivot tube 60 may also be used to accommodate wiring (not shown) to arm 22. Rotation of tube 60 and, therefore, arm 22 is limited by a screw 69 which engages a stop 71 at a desired limit of rotation.

As further shown in FIG. 2 and 2A, counterbalancing springs 70a and 70b help to counterbalance any weight being supported on second arm 22, or on an additional arm attached thereto, in a generally conventional manner. Specifically, springs 70a and 70b are connected to an adjustment screw 72 to allow adjustment of the counterbalancing force. Ends 74a, 74b are each connected to a pin which includes an internally threaded bore receiving the adjustment screw 72. The opposite ends of springs 70a and 70b are connected to pivot pin 34.

Still referring to FIG. 2, a locking mechanism 90 operates to lock each of the above described pivot connections in place after mechanism 10 has been adjusted vertically and rotationally to the desired orientation. Locking mechanism 90 is operated by a lever 92 which may be moved in a simple and short push or pull manner in a direction extending along the length of first support arm 20 as generally shown by arrow 94. Lever 92 is connected by a pivot 96 to link member 26 and is further connected to a connecting link 98 by a pin 100 extending from connecting link 98 and into a slot 102 contained in the end of lever 92. Connecting link 98 is pivotally attached at opposite ends to respective short links 104, 106 by respective pivots 108, 110. The opposite end of each short link 104, 106 is connected to rotate a respective screw 112, 114. As will be described below, these screws operate to simultaneously lock pivot connections 46 and 48 as well as the general pivot connection formed by pivots 28, 30, 32, 34 allowing arm 20 to move vertically with respect to base member 31.

Referring now to FIG. 3, to lock pivot connection 48 in place, a clamp member 116 is provided around pivot tube 60. Thus, it will be appreciated that when clamp member 116 is tightened against pivot tube 60, pivot tube 60 will not be capable of rotating and, therefore, second arm 22 will not be capable of rotating with respect to first arm 20. As more specifically shown in FIG. 3, clamp member 116 includes a first portion 118 having an internally threaded insert 120 and a second portion 122 having a hole 124. Threaded insert 120 receives a threaded portion 112a of screw 112, while hole 124 receives an unthreaded portion 112b of screw 112 with clearance to allow rotation of screw 112. Preferably, the threaded portion 112a is a double helical thread. Most preferably, screws 112, 114 are ⅜"—10 double lead screws. Additional clamp members 126, 128 are provided for locking the above described vertical movement of first arm 20 with respect to base member 31 (FIG. 2). These clamp members 126, 128 each include flange portions 126*a*, 128*a* that serve to clamp links 36*a*, 36*b* and 38*a*, 38*b* against a portion of pivot support 58 to prevent any movement of links 36*a*, 36*b* and 38*a*, 38*b* and thereby prevent any vertical movement of first arm 20 with respect to base member 31 (FIG. 2). It will further be appreciated that in an unlocked state, tubular portions 126*b*, 128*b* act as guides that ride within slots 42*a*, 42*b* and 44*a*, 44*b* during the vertical movement of first arm 20 with respect to base member 31. The tubular portion 128*b* is preferably internally threaded and carries threaded member 130 to provide adjustment capability and a force bearing surface. Washers 134, 136 are located about tubular portion 126*b* and between pivot support 58 and link member 36*b* and link members 36*a* and 36*b*. Likewise, washers 138, 140 are located between pivot support 58 and link 38*b* and links 38*a*, 38*b*.

Figure 4:
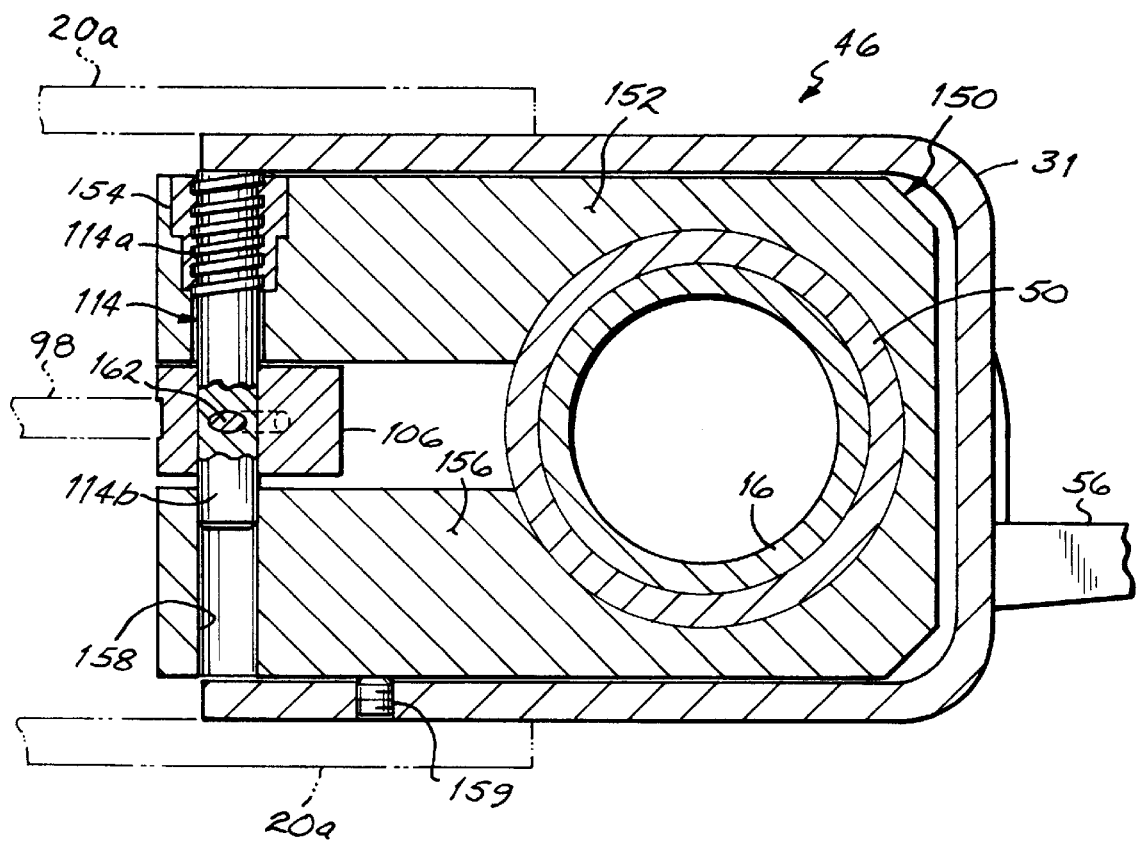
FIG. 4 is a cross sectional view taken along line 4—4 of FIG. 2.

Turning now to FIG. 4, pivot connection 46 more specifically comprises a clamp member 150 having a first portion 152 with a threaded insert 154 and a second portion 156 with a hole 158. In a manner similar to pivot connection 48, threaded insert 154 contains a double helically threaded portion 114*a* of screw 114 and hole 158 receives an unthreaded portion 114*b* of screw 114 with clearance to allow rotation of screw 114. Clamp member 150 is disposed about tube 50 and, therefore, when clamp member 150 is tightened, no rotation of base member 31 about tube 50 may take place. A set screw 159 allows adjustment in the clamping action. As further shown in both FIGS. 3 and 4, short links 104, 106 are rigidly connected to screws 112, 114 at intermediate locations thereon with retainer pins 160, 162.

Figure 5:
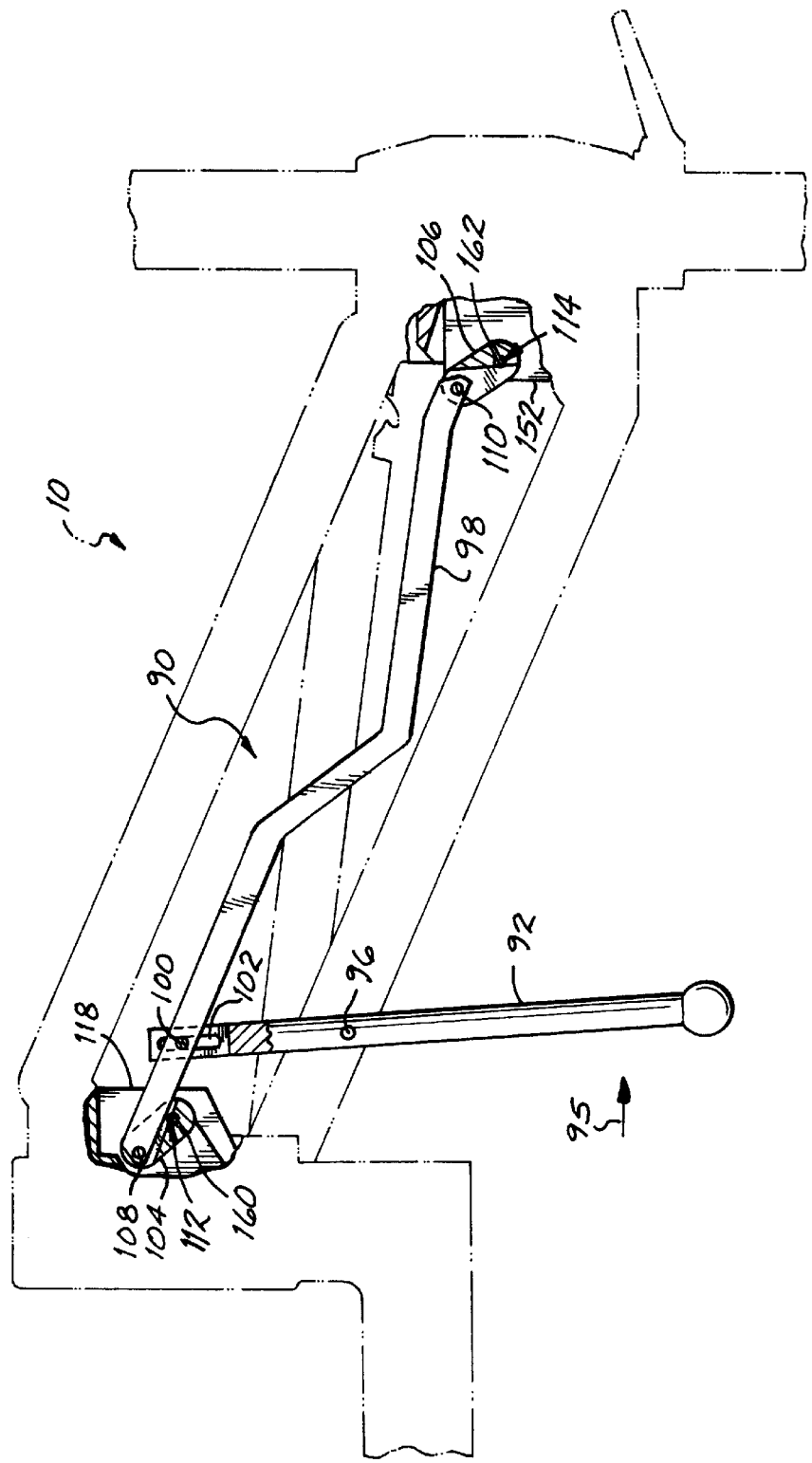
FIG. 5 is a diagrammatic view of the mechanism shown in FIG. 2 but illustrating an unlocked position.

Thus, a review of FIGS. 2–4 will indicate that moving lever 92 away from base member 31 in the direction of arrow 94 will result in connecting member 98 moving toward base member 31 and short links 104, 106 rotating screws 112, 114 clockwise as viewed in FIG. 2. As shown in FIG. 3, this will cause screw 112 to move in the direction of arrow 163 to urge clamp member 126 against links 36*a*, 36*b* until they are wedged against washers 134, 136 and pivot support 58. This will lock up and down motion of first arm 20 with respect to base member 31 (FIG. 1). Simultaneously, clamp 116 will be rotated slightly around pivot tube 60 and move generally in the direction of arrows 164, 165. This will urge clamp member 128 against links 38*a*, 38*b* and clamp these links against washers 138, 140 and against pivot support 58 to further assist in locking vertical movement of arm 20. As clamp portion 118 moves further toward clamp portion 122, pivot tube 60 is locked against any rotational movement. As long as short links 104, 106 (FIG. 2) are maintained in the position shown, mechanism 10 will be locked completely in place by the friction of screws 112, 114. To unlock mechanism 90, lever 92 is moved in the direction of arrow 95 toward base member 31 (FIG. 5). This moves short links 104, 106 to an oppositely angled position and rotates screws 112, 114 counterclockwise to reverse and unlock the various clamping movements discussed above.

Figure 6:
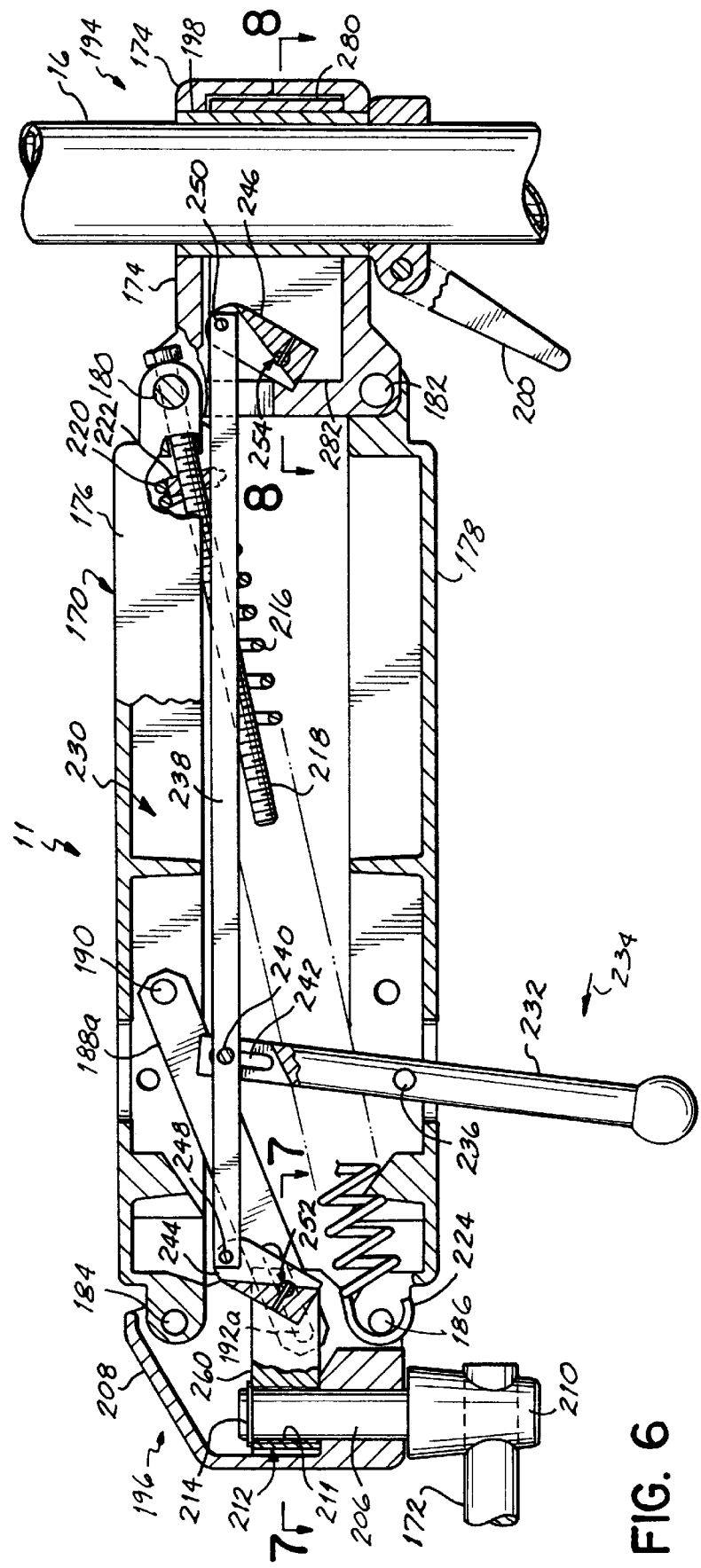
FIG. 6 is a partially fragmented side elevational view of the light duty instrument support mechanism shown in FIG. 1 showing the mechanism in a locked position.

Referring now to FIG. 6, the lighter duty instrument support mechanism 11 is shown in more detail. Mechanism 11 works on very similar principles to those discussed above with respect to mechanism 10. Mechanism 11 comprises a first arm 170 and second arm 172 which are pivotally connected to one another in a manner to be described below. First arm 170 may have a cover 170*a* (FIG. 7) to conceal internal components. First arm 170 is also pivotally connected to a base member 174 to allow vertical, pivoting movement with respect thereto as will also be described below. First arm 170 comprises a first link member 176 and a second link member 178. First and second link members 176, 178 are connected to base member 174 by respective pivots 180, 182 which allow vertical pivoting motion with respect to base member 174 in a vertical orientation as shown in FIG. 6, i.e., when support pole 16 extends in a vertical orientation. Links 188*a*, 188*b* are connected at a pivot 190 to first link member 176 as shown in FIG. 6. As further shown in FIG. 7, links 188*a*, 188*b* include respective slots 192*a*, 192*b* for reasons similar to those described above with respect to mechanism 10 as will be described in more detail below.

Again referring to FIG. 6, in addition to the pivot connections allowing generally vertical movement of the outer end of first arm 170 with respect to base member 174, pivot connections 194, 196 are provided to respectively allow pivoting motion of mechanism 11 about support pole 16 and pivoting motion of second arm 172 with respect to first arm 170. For height adjustment, like the first embodiment, a tubular support member 198 is provided to hold mechanism 11 on support pole 16 and may be locked in place by a conventional screw locking clamp mechanism 200 when positioned at the desired height along pole 16.

Figure 7:
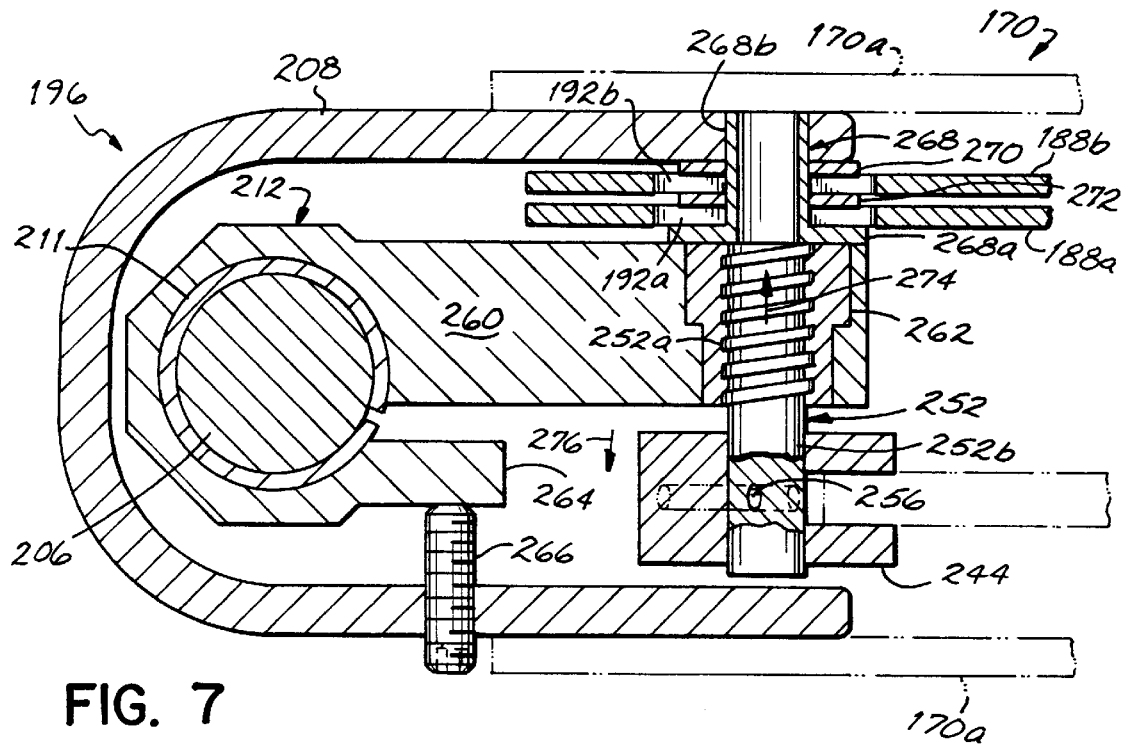
FIG. 7 is a cross sectional view taken along line 7—7 of FIG. 6.

Referring now to FIGS. 6 and 7, pivot connection 196 more specifically comprises a cylindrical rod 206 received within a pivot support or housing 208 and connected to second arm 172 by a connecting member 210. As best shown in FIG. 7, cylindrical rod 206 is preferably contained within a low friction sleeve or bearing member 211 which, in turn, is disposed within a clamp member 212. As further shown in FIG. 6, a retainer 214 keeps the cylindrical rod 206 held within pivot support or housing 208. Link members 176, 178 of first arm 170 are attached to housing 208 by pivots 184, 186.

Still referring to FIG. 6, like the first embodiment, a counterbalancing spring 216 is preferably provided and connected to an adjustment screw 218 at one end for allowing adjustment in the counterbalancing force to be made upon initial assembly or by the user. One end 220 of spring 216 is connected to a threaded member 222 which receives adjustment screw 218 for threaded adjustment therein. The other end 224 of spring 216 is connected to pivot pin 186.

As further shown in FIG. 6, a locking mechanism 230 is provided for locking the various pivot connections of arm 11. Locking mechanism 230 is similar to locking mechanism 90 of instrument support mechanism 10. Specifically, a lever 232 operates generally in the direction of arrow 234 to lock pivot connections 194 and 196 as well as the general pivot connection made between base member 174 and first arm 170 which allows vertical adjustment of first arm 170 with respect to base member 174. More specifically, lever 232 is connected by a pivot 236 to second link member 178 and is further connected to a connecting link by a pin 240 extending therefrom and into a slot 242 in the end of lever 232. Short links 244, 246 are connected at respective ends of connecting link 238 by pivots 248, 250. The opposite end of each short link 244, 246 is rigidly affixed to respective screws 252, 254 by retainer pins 256, 258. Thus, it will be appreciated that when lever is pulled away from base member 174 to the position shown in FIG. 6, short links 244, 246 will rotate screws 252, 254 clockwise to simultaneously lock the various pivot connections as will be described. Preferably, screws 252, 254 are each ⅜"—10 double lead screws.

Referring now more specifically to FIG. 7, the locking mechanism 230 preferably operates clamp member 212 to selectively allow or prevent rotation of cylindrical rod 206.

Specifically, a first portion 260 of clamp member 212 includes a threaded insert 262 for receiving threaded portion 252a of screw 252. A second portion 264 of clamp member 212 interacts with an adjustable screw stop 266. Finally, similar to the first embodiment, a clamp member 268 including a flange portion 268a and a tubular portion 268b is operated by one end of screw 252 to selectively allow and prevent movement of links 188a, 188b. As also provided in the first embodiment, washers 270, 272 are respectively disposed between pivot support housing 208 and link 188b and between links 188a and 188b. Thus, when screw 252 is rotated by short link 244 to move in the direction of arrow 274, clamp member 268 will move upwardly as viewed in FIG. 7 and flange portion 268a will clamp links 188a, 188b against washers 270, 272 and the inside of pivot support or housing 208. This will prevent movement of links 188a, 188b by way of slots 192a, 192b riding along tubular clamp portion 268b and thereby prevent any articulating up and down movement of first arm 170 (FIG. 6). At the same time, portion 260 of clamp member 212 will move generally in the direction of arrow 276 and, as portion 264 is stopped against threaded stop member 266, this will clamp cylindrical pivot rod 206 against any rotation.

Figure 8:
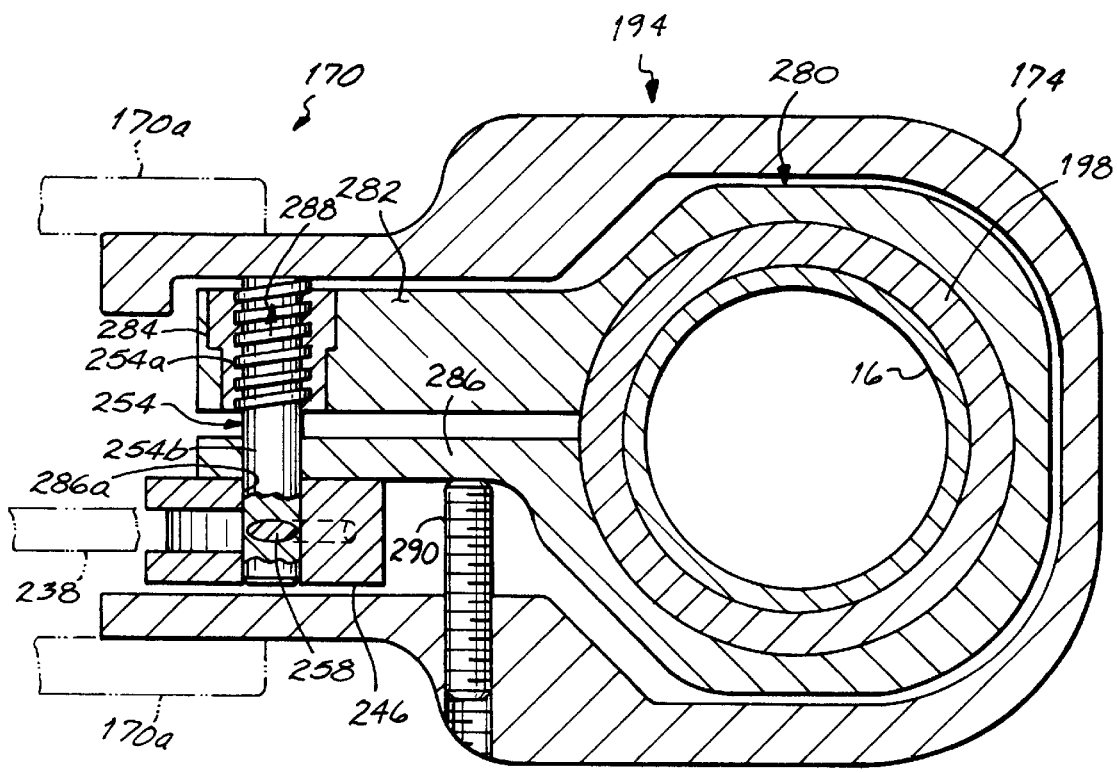
FIG. 8 is a cross sectional view taken along line 8—8 of FIG. 6.

Referring now to FIG. 8, a clamp member 280 is provided at the opposite end of first arm 170 to selectively allow or prevent rotation of first arm 170 and any attachments about support pole 16. Specifically, clamp member 280 includes a first portion 282 having a threaded insert 284 for receiving threaded portion 254a of screw 254. A second portion 286 of clamp member 280 includes a hole 286a which receives an unthreaded portion 254b of screw 254 with clearance for rotation. Thus, when short link 246 is rotated by connecting link 238 in a clockwise direction as viewed in FIG. 6, screw 252 will move in the direction of arrow 288 and bear against the inside of base member 174. This will cause portion 282 of clamp member 280 to move in an opposite direction and, as portion 286 bears against adjustment screw 290, a clamping action will take place against tubular support member 198. Like the other adjustment screws, screw 290 allows adjustment in the clamping action. Therefore, base member 174 will not be able to rotate about tubular support member 198.

Figure 9:
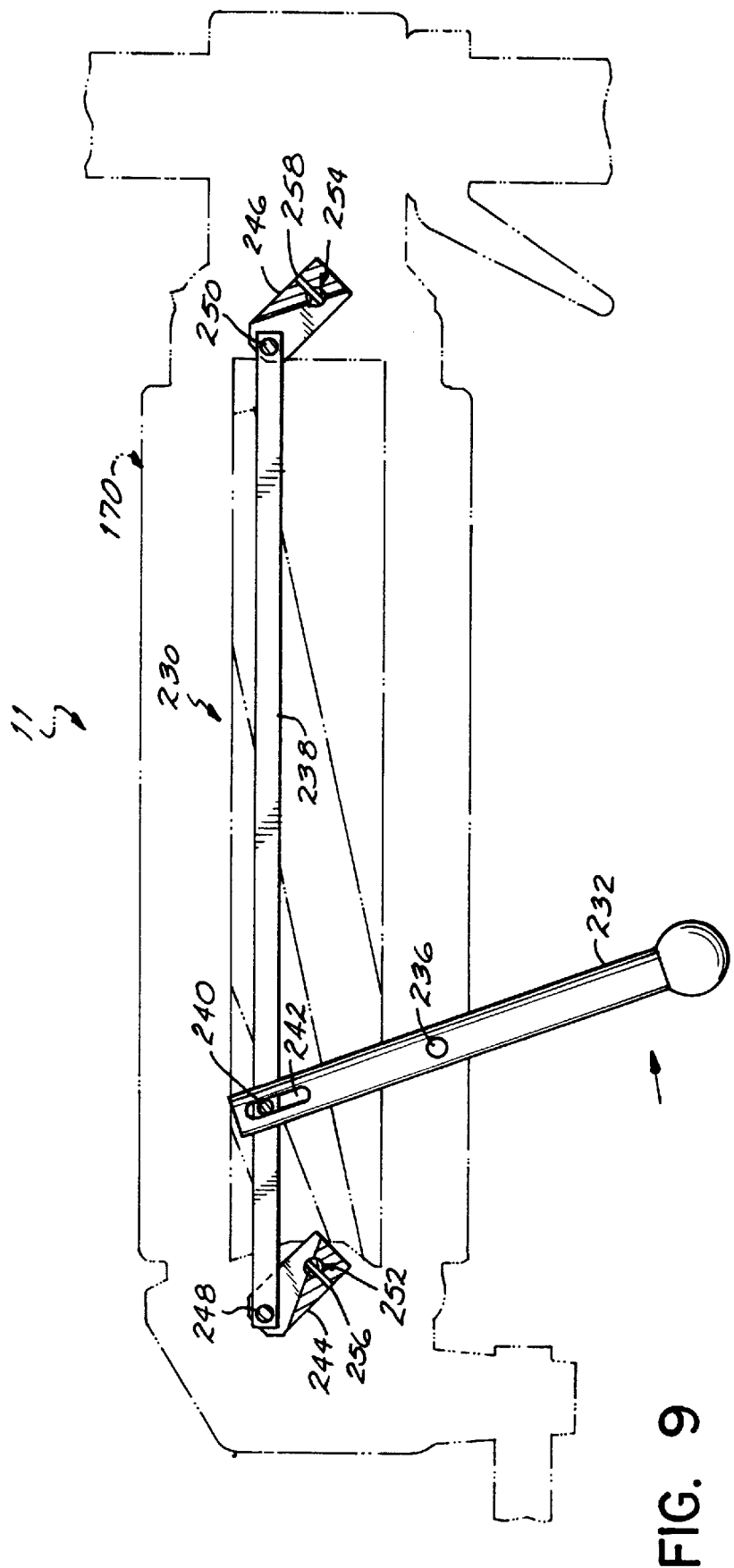
FIG. 9 is a diagrammatic view of the mechanism shown in FIG. 6 but illustrating an unlocked position.

Generally referring to FIGS. 6–8, and to summarize the operation of mechanism 11, when lever 232 is pulled in the direction of arrow 234 away from base member 174, short links 244, 246 will be rotated by connecting link 238 and thereby rotate screws 252, 254 in a clockwise direction as viewed in FIG. 6. As shown in FIG. 7, this will move screw 252 in the direction of arrow 274 to clamp links 188a, 188b against any movement and further move first clamp portion 260 in the direction of arrow 276 to prevent any rotational movement of pivot rod 206. In this manner, pivoting of second arm 172 with respect to first arm 170 is prevented and vertical movement of first arm 170 with respect to base member 174 is also prevented. At the same time and referring more specifically to FIG. 8, screw 254 will be moved in the direction of arrow 288 and thereby clamp member 280 against support tube 198 in the manner described above to prevent any rotational movement of mechanism 11 about support pole 16. As schematically shown in FIG. 9, movement of lever 232 in an opposite direction toward pole 16 will rotate screws 252, 254 in a counterclockwise direction thereby unlocking all of the pivot connections described above and allowing readjustment of mechanism 11 to a desired position.

While the present invention has been illustrated by a description of various embodiments and while these embodiments have been described in considerable detail, it is not the intention of the Applicant to restrict or in any way limit the scope of the appended claims to such detail. As an example, the various features of the mechanisms described herein in detail may be combined or substituted in various manners. Additional advantages and modifications will readily appear to those skilled in the art. The invention in its broader aspects is therefore not limited to the specific details, representative apparatus and methods as shown and described. This has been a description of the present invention, along with the preferred methods of practicing the present invention as currently known. However, the invention itself should only be defined by the appended claims, wherein

We claim:

1. A medical instrument support mechanism comprising:
   a base member;
   a first support arm having first and second ends and a length therebetween, the first end being connected to the base member by a first pivot connection allowing the second end to be raised and lowered relative to the base member;
   a second support arm connected to the first support arm by a second pivot connection to allow the second support arm to swing about an axis relative to the first support arm; and
   a locking mechanism operatively connected to both the first and second pivot connections to allow an operator to selectively lock and unlock the first and second pivot connections, the locking mechanism being operated by a lever movable in a direction extending along the length of the first support arm.

2. The medical instrument support mechanism of claim 1, wherein the base member is connected to a support pole by a third pivot connection allowing rotation of the base member relative to the pole.

3. The medical instrument support mechanism of claim 2, wherein the locking mechanism is further connected to the third pivot connection and the lever further operates to lock and unlock the third pivot connection simultaneously with the first and second pivot connections.

4. The medical instrument support mechanism of claim 3, wherein the second and third pivot connections are locked and unlocked by screws which form part of the locking mechanism.

5. The medical instrument support mechanism of claim 4, wherein the base member is further connected to the support pole in a manner allowing height adjustment along the support pole.

6. The medical instrument support mechanism of claim 1, wherein the second support arm is connected to a medical instrument.

7. The medical instrument support mechanism of claim 6, wherein the medical instrument is one of an optical or ophthalmological instrument.

8. The medical instrument support mechanism of claim 6, wherein the base member is connected for height adjustment along a support pole.

9. The medical instrument support mechanism of claim 1, wherein the locking mechanism further includes a screw that rotates to locked and unlocked positions to respectively prevent and allow operation of the first and second pivot connections.

10. The medical instrument support mechanism of claim 9, wherein the screw includes double helical threads.

11. The medical instrument support mechanism of claim 9, wherein the first pivot connection includes at least one movable link and the second pivot connection includes a clamp member, and the screw operates to selectively allow and prevent movement of the link and selectively clamp and unclamp the clamp member to lock and unlock the first and second pivot connections.

12. The medical instrument support mechanism of claim 11, wherein the movable link is pivotally connected generally between the first and second support arms and the clamp member is connected to the first support arm and receives a portion of the second support arm for rotation therein.

13. A medical instrument support mechanism comprising:
a base member;
a first support arm having first and second ends with a length therebetween, the first end being connected to the base member by a first pivot connection such that the first support arm may be rotated about an axis relative to the base member; and
a locking mechanism operatively connected to the pivot connection to allow an operator to selectively lock and unlock the first pivot connection, wherein the locking mechanism includes a lever disposed on an underside of the first support arm and the lever is movable in a direction extending along the length of the first support arm to selectively lock and unlock the first pivot connection.

14. The medical instrument support mechanism of claim 13 further comprising a second support arm connected to the first support arm by a second pivot connection to allow the second support arm to swing about an axis relative to the first support arm, and wherein the locking mechanism simultaneously controls operation of both the first and second pivot connections by respective movements of the lever.

15. The medical instrument support mechanism of claim 14, wherein the second support arm is connected to one of an optical instrument and an ophthalmological instrument.

16. The medical instrument support mechanism of claim 14, wherein the base member is connected to a support pole by a third pivot connection.

17. The medical instrument support mechanism of claim 16, wherein the base member is further connected to the support pole in a manner allowing adjustment along the support pole.

18. The medical instrument support mechanism of claim 16, wherein the locking mechanism is further connected to the third pivot connection to lock and unlock the third pivot connection simultaneously with the first and second pivot connections.

19. The medical instrument support mechanism of claim 18, wherein the third pivot connection is made with the base member receiving the support pole in a manner allowing rotation of the base member about the support pole.

20. The medical instrument support mechanism of claim 19, wherein the locking mechanism further includes a screw that rotates to locked and unlocked positions relative to the first and third pivot connections.

21. The medical instrument support mechanism of claim 20, wherein the first pivot connection includes at least one movable link and the third pivot connection includes a clamp member, and the screw operates to selectively allow and prevent movement of the link and selectively clamp and unclamp the clamp member to respectively lock and unlock the first and third pivot connections.

22. The medical instrument support mechanism of claim 21, wherein the movable link is pivotally connected between the first and second support arm and the clamp member is connected to the first support arm and receives a portion of the second support arm for rotation.

23. The medical instrument support mechanism of claim 13, wherein the base member is connected for adjustment along a support pole.

24. The medical instrument support mechanism of claim 13, wherein the lever moves in a direction away from the base member to lock the first pivot connection.

25. A medical instrument support mechanism comprising:
a base member;
a first support arm having first and second ends and a length therebetween, the first end being connected to the base member by a first pivot connection;
a second support arm connected to the first support arm by a second pivot connection;
linkage members operatively connected between the base member and the first support arm for allowing the second end to be moved vertically with respect to the base member; and
first and second screw locking mechanisms operatively connected to the first and second pivot connections and to the linkage members and operated by a single actuator member to selectively lock and unlock the first and second pivot connections and selectively allow and prevent vertical movement of the first support arm.

26. The medical instrument support mechanism of claim 25, wherein the screw locking mechanism includes first and second screws disposed transversely to the first support arm at the respective first and second ends, each screw operating a respective clamp member connected with the two pivot connections.

27. The medical instrument support mechanism of claim 26, wherein one of the screws is operatively connected to the linkage members to selectively allow and prevent movement thereof.

28. The medical instrument support mechanism of claim 26, wherein the screws have double helical threads.

29. The medical instrument support mechanism of claim 25, wherein the actuator member is a lever operatively connected to the first and second screws.

30. The medical instrument support mechanism of claim 29, wherein the lever moves in a direction extending along the length of the first support arm.

31. The medical instrument support mechanism of claim 30, wherein the lever is disposed along a lower side of the first support arm.

32. The medical instrument support mechanism of claim 31, wherein the lever moves in a direction away from the base member to lock the first and second pivot connections and to prevent vertical movement of the second end of the first support arm.

33. A medical instrument support mechanism comprising:
a base member;
a first support arm having first and second ends and a length therebetween, the first end being connected to the base member by a first pivot connection allowing the second end to be moved with respect to the base member; and
a locking mechanism operatively connected to the first pivot connection to allow an operator to selectively lock and unlock the first pivot connection, the locking mechanism being operated by a lever connected along a lower surface of the first support arm and movable in a direction extending along the length of the first support arm.

34. The medical instrument support mechanism of claim 33 further comprising a second support arm connected to the first support arm by a second pivot connection to allow the second support arm to swing about an axis relative to the first support arm, and wherein the locking mechanism simultaneously controls operation of both the first and second pivot connections by respective movements of the lever.

35. The medical instrument support mechanism of claim 34, wherein the second support arm is connected to one of an optical instrument and an ophthalmological instrument.

36. The medical instrument support mechanism of claim 35, wherein the base member is connected to a support pole by a third pivot connection.

37. The medical instrument support mechanism of claim 35, wherein the locking mechanism is further connected to the third pivot connection to lock and unlock the third pivot connection simultaneously with the first and second pivot connections.

38. The medical instrument support mechanism of claim 34, wherein the third pivot connection is made with the base member receiving the support pole in a manner allowing rotation of the base member about the support pole.

39. The medical instrument support mechanism of claim 38, wherein the locking mechanism further includes a screw that rotates to locked and unlocked positions relative to the first and third pivot connections.

* * * * *